United States Patent
Matula (10) Patent No.: US 11,399,797 B2
(45) Date of Patent: Aug. 2, 2022

(54) STETHOSCOPE ACOUSTIC TUBING THAT IS DISCONNECTABLE INTO SEPARATE SEGMENTS

(71) Applicant: Small Business Consulting Strategic Marketing, LLC, Houston, TX (US)

(72) Inventor: Sean Matula, Houston, TX (US)

(73) Assignee: SMALL BUSINESS CONSULTING STRATEGIC MARKETING, LLC, Houston, TX (US)

( * ) Notice: Subject to any disclaimer, the term of this patent is extended or adjusted under 35 U.S.C. 154(b) by 293 days.

(21) Appl. No.: 16/851,226

(22) Filed: Apr. 17, 2020

(65) Prior Publication Data
US 2021/0321972 A1 Oct. 21, 2021

(51) Int. Cl.
*A61B 7/02* (2006.01)
*G10K 13/00* (2006.01)
*G10K 11/08* (2006.01)

(52) U.S. Cl.
CPC .............. *A61B 7/02* (2013.01); *G10K 11/08* (2013.01); *G10K 13/00* (2013.01); *A61B 2560/0456* (2013.01); *A61B 2562/225* (2013.01)

(58) Field of Classification Search
CPC .............. A61B 7/02; A61B 2562/225; A61B 2560/0456; G10K 11/08; G10K 13/00
See application file for complete search history.

(56) References Cited

U.S. PATENT DOCUMENTS

| | | | | |
|---|---|---|---|---|
| 2,807,328 A | * | 9/1957 | Gould | A61B 7/02 D24/134 |
| 3,766,361 A | * | 10/1973 | Swinyar | A61B 90/00 248/314 |
| 4,064,965 A | * | 12/1977 | Brown | A61B 7/02 181/135 |
| 4,633,971 A | * | 1/1987 | Robbins | A61B 7/02 181/135 |
| 5,650,598 A | * | 7/1997 | Abelson | A61B 7/02 181/131 |
| 5,798,489 A | * | 8/1998 | Gillio | A61B 7/02 181/131 |
| 5,945,641 A | * | 8/1999 | Shieh | A61B 7/02 181/131 |
| D425,353 S | * | 5/2000 | Foy | D24/134 |

(Continued)

*Primary Examiner* — Jeremy A Luks
(74) *Attorney, Agent, or Firm* — Jeffrey Streets; Madan Law (57) ABSTRACT

A stethoscope includes a headset including a first eartube terminating in a first earpiece and a second eartube terminating in a second earpiece, and a chestpiece having a diaphragm. The stethoscope further includes flexible acoustic tubing having a first tubing segment connected to the headset and a second tubing segment connected to the chestpiece. The first tubing segment is manually disconnectable from the second tubing segment, and the first tubing segment is manually connectable to the second tubing segment to align and seal the first and second tubing segments and form an acoustic passageway extending from the chestpiece through the first and second tubing segments and the first and second eartubes to the first and second earpieces. Optionally, the flexible acoustic tubing with the disconnectable and connectable segments may be provided as a replacement component for a stethoscope.

16 Claims, 10 Drawing Sheets

(56) References Cited

U.S. PATENT DOCUMENTS

| | | | | |
|---|---|---|---|---|
| 6,484,918 B1* | 11/2002 | Lefebvre | ............... | A61B 7/02 |
| | | | | 224/678 |
| 7,516,814 B1* | 4/2009 | Berk | ............... | A61B 7/026 |
| | | | | 600/528 |
| D618,345 S * | 6/2010 | Baker | ............... | D24/134 |
| 7,841,445 B2* | 11/2010 | Berk | ............... | A61B 7/026 |
| | | | | 600/528 |
| 2004/0226771 A1* | 11/2004 | Werblud | ............... | A61B 7/02 |
| | | | | 181/131 |
| 2016/0324996 A1* | 11/2016 | Bilenko | ............... | A61L 2/24 |
| 2018/0200396 A1* | 7/2018 | Messina | ............... | A61L 2/10 |
| 2019/0150880 A1* | 5/2019 | Campbell | ............... | A61L 2/04 |

\* cited by examiner

STETHOSCOPE ACOUSTIC TUBING THAT IS DISCONNECTABLE INTO SEPARATE SEGMENTS

BACKGROUND

The present disclosure relates to stethoscopes, such as those used by medical professionals to diagnose the condition of their patients.

BACKGROUND OF THE RELATED ART

A stethoscope is an acoustic device that facilitates listening to sounds within an object in situations where the sound may be otherwise difficult to hear. Furthermore, a stethoscope may be used to listen to sounds with a comfortable separation between the listener and the object that is producing the sounds. In one example, a mechanic may use a stethoscope to listen to sounds within an engine, transmission, differential or bearing that is located in a physically constricted location of an automobile, such that the mechanic is prevented from pressing their ear against the object. In another example, a doctor, nurse, emergency responder, veterinarian or other medical professional may use a stethoscope to listen to sounds produced by a patient's organs while maintaining a comfortable separation between the medical professional and the patient.

A stethoscope is designed to pick up body sounds through vibrations and transmit them to the ears of the user. A conventional stethoscope includes a chestpiece having a drum that secures a diaphragm. As sound from a body reaches the diaphragm, the diaphragm vibrates and amplifies the sound. The sound is then transmitted through a section of sealed hollow acoustic tubing to the earpieces that fit in the user's ears. Some stethoscopes have a dual-headed chestpiece, which includes the diaphragm on one side for listening to high-frequency vibrations and a small bell on the opposing side for listening to low-frequency vibrations.

Medical professionals may use a stethoscope for evaluating numerous conditions of a patient. In a patient evaluation, the medical professional may listen to the patient's heart, lungs, intestines, and the like. When listening to a patient's heart, the medical professional may listen to the heart by placing the diaphragm against the patient's chest in multiple locations to listen to heart muscle contractions in each of the heart chambers and listen to the operation of each of the heart valves. Similarly, when listening to a patient's lungs, the medical professional may place the diaphragm against the patient's chest and back in multiple locations to listen to air flow in and out of the various regions of the lungs.

BRIEF SUMMARY

Some embodiments provide a stethoscope comprising a headset including a first eartube terminating in a first earpiece and a second eartube terminating in a second earpiece, and a chestpiece having a diaphragm. The stethoscope further comprises flexible acoustic tubing having a first tubing segment connected to the headset and a second tubing segment connected to the chestpiece. The first tubing segment is manually disconnectable from the second tubing segment, and the first tubing segment is manually connectable to the second tubing segment to align and seal the first and second tubing segments and form an acoustic passageway extending from the chestpiece through the first and second tubing segments and the first and second eartubes to the first and second earpieces.

Some embodiments provide a replacement component for a stethoscope. The replacement component comprises flexible acoustic tubing having a first tubing segment connectable to a headset of the stethoscope and a second tubing segment connectable to a chestpiece of the stethoscope. The first tubing segment is manually disconnectable from the second tubing segment, and the first tubing segment is manually connectable to the second tubing segment to align and seal the first and second tubing segments and form an acoustic passageway extending through the first and second tubing segments.

Some embodiments provide a conversion kit for modifying a conventional stethoscope so that the acoustic tubing includes a first tubing segment connected to the headset that is disconnectable from, and connectable to, a second tubing segment connected to the chestpiece. For example, the conversion kit may include a first connector component and a second connector component, wherein the first and second connector components each have an acoustic passageway extending there through. The first connector component is manually connectable to, and manually disconnectable from, the second connector component. A conventional stethoscope may be modified by cutting the acoustic tubing at a desired location so that the acoustic tubing then includes a first tubing segment and a second tubing segment. The first connector component may then be secured to the first tubing segment and the second connector component may be secured to the second tubing segment.

Some embodiments provide a kit comprising a cradle having a back wall for securing to a flat vertical surface, an open top, and a slot extending down a center of a front wall and along a bottom wall at least partially toward the back wall of the cradle, wherein the cradle is sized to receive a chestpiece having a stem and connected acoustic tubing segment, and wherein the cradle allows the stem and the acoustic tubing segment to extend through the slot and hang downwardly from the cradle. The kit further comprises a stethoscope, where the stethoscope comprises a headset including a first eartube terminating in a first earpiece and a second eartube terminating in a second earpiece, and a chestpiece having a diaphragm. The stethoscope further comprises flexible acoustic tubing having a first tubing segment connected to the headset and a second tubing segment connected to the chestpiece, wherein the first tubing segment is manually disconnectable from the second tubing segment, and wherein the first tubing segment is manually connectable to the second tubing segment to align and seal the first and second tubing segments and form an acoustic passageway extending from the chestpiece through the first and second tubing segments and the first and second eartubes to the first and second earpieces.

DETAILED DESCRIPTION

Some embodiments provide a stethoscope comprising a headset including a first eartube terminating in a first earpiece and a second eartube terminating in a second earpiece, and a chestpiece having a diaphragm. The stethoscope further comprises flexible acoustic tubing having a first tubing segment connected to the headset and a second tubing segment connected to the chestpiece. The first tubing segment is manually disconnectable from the second tubing segment, and the first tubing segment is manually connectable to the second tubing segment to align and seal the first and second tubing segments and form an acoustic passageway extending from the chestpiece through the first and second tubing segments and the first and second eartubes to the first and second earpieces.

Conventional stethoscopes suffer a technical problem in that the chestpiece makes contact with the skin of the patient and can become contaminated with bacteria, fungus, viruses or any other contaminant that may be on the skin. For example, if the patient has a virus and has coughed recently, the virus may contact the skin and survive on the skin for a period of time. Accordingly, there is potential for the chestpiece to become contaminated with the virus during a patient examination. This contamination can be spread from patient to patient as a medical professional uses their stethoscope on a series of patients. A chestpiece may be cleaned and/or disinfected between patient examinations, but this requires constant diligence. Similarly, medical professionals will typically not share a stethoscope in order to always have a stethoscope available and to avoid sharing their own germs and contaminants that may be present on the earpieces and/or other surfaces that may become contaminated. Embodiments described herein solve these technical problems by providing a stethoscope that is manually disconnectable into separate first and second tubing segments, and manually connectable to align and seal the first and second tubing segments and form an acoustic passageway extending from the chestpiece through the first and second tubing segments and the first and second eartubes to the first and second earpieces. Using these embodiments opens up the possibility of various new practices having a reduced possibility of spreading a contaminant among patients and medical professionals. One non-limiting example of such a new practice includes dedicating each stethoscope headset to a particular medical professional and dedicating each stethoscope chestpiece to a particular patient. The benefits of this practice are high in a hospital setting where the patient must be examined frequently and perhaps by more than one medical professional. A chestpiece may be left in the patient room or attached to the patient bed for use only with the particular patient, while the medical professional will always use the same headset. In some examples, neither the headset nor the chestpiece need be cleaned or disinfected following a patient examination, yet the threat of spreading contamination has been dramatically reduced or eliminated.

The first tubing segment and the second tubing segment may connect and disconnect at any point along the length of the flexible acoustic tubing. Depending upon the application of the stethoscope, it may be desirable to be able to disconnect the flexible acoustic tubing near to the headset, near to the chestpiece, or at some intermediate point along the length of the flexible acoustic tubing. Optionally, the flexible acoustic tubing may be separated into two or more segments, where each segment is disconnectable and connectable to an adjacent segment. For example, a flexible acoustic tube that is branched (i.e., has Y-shaped acoustic tubing) may be disconnectable and connectable in each of the two branches leading to the eartubes, such that the flexible acoustic tubing would include three tubing segments. Furthermore, a non-branched portion of the flexible acoustic tubing may also be disconnectable and connectable in multiple locations in series along its length. In some embodiments, the flexible acoustic tubing may be made with neoprene, silicone and/or polyvinylchloride (PVC).

In some embodiments, the first tubing segment may be branched. A branched first tubing segment may include a first proximal end connected to the first eartube, a second proximal end connected to the second eartube, and a distal end that is disconnectable from, and connectable to, the second tubing segment.

In some embodiments, the first tubing segment has a first magnetic element embedded in a distal end of the first tubing segment, and the second tubing segment has a second magnetic element embedded in a proximal end of the second tubing segment. The first and second magnetic elements impart a magnetic pull there between, which forms the connection between the first and second tubing segments. The first and second magnetic elements may also be embedded in positions so that the magnetic pull will both align and seal the distal end of the first tubing segment to the proximal end of the second tubing segment. For example, if the first and second magnetic elements are both rings axially centered with respect to the axial centerline of the flexible acoustic tubing, then the magnetic pull should bias the first and second tubing segments to be axially aligned with each other. Furthermore, with the magnetic elements embedded within the flexible acoustic tubing material, the opposing circular contact surfaces between the first and second tubing segments will be the flexible acoustic tubing material such that a seal may be easily formed there between. Optionally, the magnetic elements may be embedded into the ends of the first and second tubing segments by injection molding the acoustic tubing material around a ring-shaped magnetic element disposed in the injection mold. Alternatively, the magnetic elements may be embedded into the ends of the first and second tubing segments by forming a ring-shaped track in the end of an acoustic tube, positioning the ring-shaped magnetic element into the track, then adhering or applying a layer of the acoustic tubing material over the circular end of the tubing segment. In embodiments that include first and second magnetic elements, at least one of the magnetic elements should be a permanent magnet. However, in some embodiments the first and second magnetic elements may both be permanent magnets, and in some other embodiments one of the first and second magnetic elements may be a permanent magnet and the other of the first and second magnetic elements may be a ferromagnetic material, such as iron, cobalt, nickel and most of their alloys.

Some embodiments may use a connector that enables the first tubing segment to be manually disconnectable and manually connectable with the second tubing segment. In other words, the user can select whether to manually connect or manually disconnect the first and second tubing segments. In one example, the first tubing segment may include a first connector component and the second tubing segment may include a second connector component. The acoustic passageway extends through the first connector component and the second connector component, and the first connector component is manually connectable to, and manually disconnectable from, the second connector component. Each connector component may have a first end that is connected to the flexible acoustic tubing material and a second end that is manually connectable to, and manually disconnectable from, a second end of the opposing connector component. For example, the first connector component may be a first fitting secured to a distal end of the first tubing segment, and the second connector component may be a second fitting secured to a proximal end of the second tubing segment. In one option, the first and second fittings may include both a male luer fitting and a female luer fitting. In another option, the first and second fittings may be mating quarter-turn fittings. In a further option, the first and second fittings may each include a magnetic element so that a magnetic pull between the first and second fittings will align and seal the distal end of the first tubing segment to the proximal end of the second tubing segment. A magnetic element may form any suitable arrangement, such as a first magnetic element that forms a first circular ring in a first fitting and a second magnetic element that forms a second circular ring in a second fitting. In any of the foregoing options, the acoustic passageway may extend through the first and second circular rings.

In some embodiments, one or more of the connector components may be a press-to-connect fitting that is connected to a tubing segment by inserting a barbed stem of the press-to-connect fitting into the passageway in the tubing segment. The barbed stem may have directionally oriented barbs, such that the tubing segment may be manually pressed onto the barbed stem with less force than required to manually remove the barbed stem from the tubing segment. In one configuration, the first connector component may be a first press-to-connect fitting secured to a distal end of the first tubing segment, and the second connector component may be a second press-to-connect fitting secured to a proximal end of the second tubing segment. Accordingly, the first press-to-connect fitting may have a barbed stem that is securely received into the distal end of the first tubing segment, and the second press-to-connect fitting may have a barbed stem that is securely received into the proximal end of the second tubing segment.

In some embodiments, one or more of the connector components may be adhesively secured to a tubing segment. For example, the first connector component may include a stem that is adhesively secured to a distal end of the first tubing segment, and the second connector component may be adhesively secured to a proximal end of the second tubing segment. Optionally, the end of a tubing segment may include a recess for receiving the stem with adhesive between the stem and the adhesive there between.

In some embodiments, the headset may form a generally circular collar for hanging around a user's neck when the second segment has been disconnected from the first segment. The circular collar of the headset may include the eartubes and a binaural spring, but they should be shaped to be generally circular in order to hang comfortably around a medical professional's neck. The generally circular collar is beneficial for keeping the headset in a convenient position for use by the medical profession. Since the headset may be disconnected from any chestpiece except during an actual patient examination, it is not possible to hang an entire stethoscope around the back of the neck and over the shoulders.

Some embodiments of the chestpiece may include a magnet that enables the chestpiece to be secured to a metal structure when the second segment has been disconnected from the first segment. For example, the chestpiece may include a continuous magnetic ring around the edge of the diaphragm of the chestpiece or one or more magnets placed near the edge of the diaphragm.

Some embodiments provide a replacement component for a stethoscope. The replacement component may comprise flexible acoustic tubing having a first tubing segment connectable to a headset of a stethoscope and a second tubing segment connectable to a chestpiece of the stethoscope. The first tubing segment may be manually disconnectable from the second tubing segment, and the first tubing segment may be manually connectable to the second tubing segment to align and seal the first and second tubing segments and form an acoustic passageway extending through the first and second tubing segments. Furthermore, the replacement component may include or incorporate any one or more of the features or details of acoustic tubing that are described in reference to any embodiment of a stethoscope. For example, the replacement component may include first and second embedded magnetic elements, first and second connector components, and the like as described herein.

Some embodiments provide a conversion kit for modifying a conventional stethoscope so that the acoustic tubing includes a first tubing segment connected to the headset that is disconnectable from, and connectable to, a second tubing segment connected to the chestpiece. For example, the conversion kit may include a first connector component and a second connector component, wherein the first and second connector components each have an acoustic passageway extending there through. The first connector component is manually connectable to, and manually disconnectable from, the second connector component. A conventional stethoscope may be modified by cutting the acoustic tubing at a desired location so that the acoustic tubing then includes a first tubing segment and a second tubing segment. The first connector component may then be secured to the first tubing segment and the second connector component may be secured to the second tubing segment. For example, each connector component may be a fitting having a first end for connecting to an end of the acoustic tubing and a second end that is disconnectable from, and connectable to, a second end of the other connector component. The first end may include a press-to-connect coupling with a barbed stem for inserting into an end of the acoustic tubing or may include a stem for adhesively securing to the acoustic tubing. The second ends of the first and second connector components may include, for example, male and female luer type connectors, male and female quarter-turn connectors, or connectors including magnetic elements. Optionally, the kit may further include one or more of a blade for cutting the conventional acoustic tubing and/or a cradle for supporting a chestpiece and a second tubing segment secured to the chestpiece.

Some embodiments provide a kit comprising a cradle having a back wall for securing to a flat vertical surface, an open top, and a slot extending down a center of a front wall and along a bottom wall at least partially toward the back wall of the cradle, wherein the cradle is sized to receive a chestpiece having a stem and connected acoustic tubing segment, and wherein the cradle allows the stem and the acoustic tubing segment to extend through the slot and hang downwardly from the cradle. The kit further comprises a stethoscope, where the stethoscope comprises a headset including a first eartube terminating in a first earpiece and a second eartube terminating in a second earpiece, and a chestpiece having a diaphragm. The stethoscope further comprises flexible acoustic tubing having a first tubing segment connected to the headset and a second tubing segment connected to the chestpiece, wherein the first tubing segment is manually disconnectable from the second tubing segment, and wherein the first tubing segment is manually connectable to the second tubing segment to align and seal the first and second tubing segments and form an acoustic passageway extending from the chestpiece through the first and second tubing segments and the first and second eartubes to the first and second earpieces. Furthermore, the kit may include or incorporate any one or more of the features or details that are described in reference to any embodiment of a stethoscope. Still further, the kit may include a plurality of chestpieces for each headset.

Figure 1:
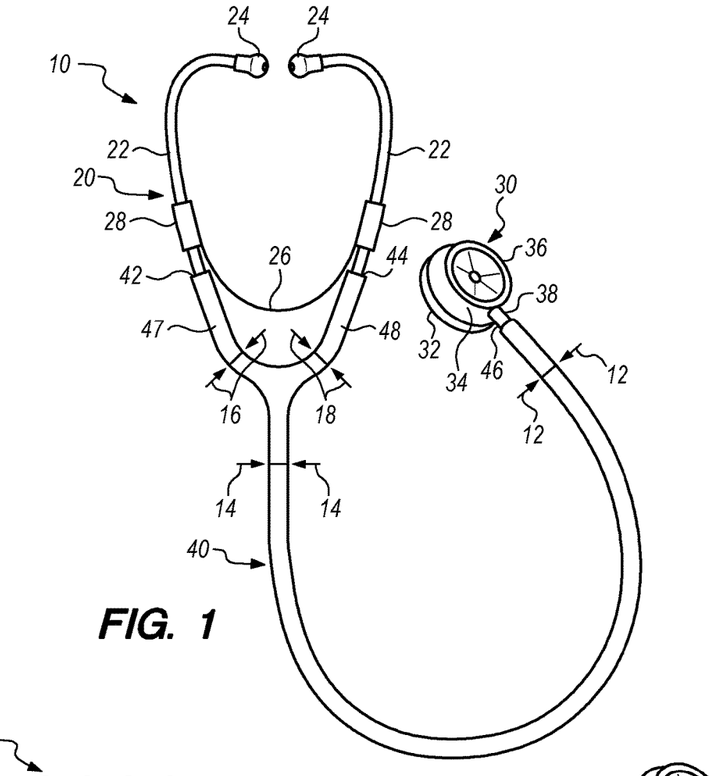
FIG. 1 is a diagram of a stethoscope.

FIG. 1 is a diagram of a stethoscope 10. The stethoscope 10 includes a headset 20, a chestpiece 30, and acoustic tubing 40 for transmitting acoustic waves ("sound") from the chestpiece 30 to the headset 20. The headset 20 includes a pair of eartubes 22, with each eartube 22 including an earpiece 24 that fits in the ear of a medical professional or other stethoscope user. The eartubes 22 are hollow tubes, typically made of metal, that connect to the acoustic tube 40 on one end and the earpieces 24 on the other end. The headset 20 also includes an optional binaural spring 26, typically made of metal, which connects the eartubes 22 and may impart a gentle bias on the eartubes 22 that keeps the earpieces 24 in the medical professional's ears so that the medical professional may use their hands for manipulating the chestpiece or other tasks. The binaural spring 26 may be secured to an eartube 22 with a binaural spring clamp 28, which may be welded to the eartube 22. The eartubes and binaural spring may be made of various materials, such as aluminum, stainless steel, titanium and/or brass.

The chestpiece 30 includes a diaphragm 32 (see FIG. 5A) on one face of a drum 34. The chestpiece 30 may also include a bell 36 which may be better suited to listening for low frequency sounds. A hollow stem 38 extends from the drum 34 and provides a means for connecting the chestpiece to the acoustic tubing 40. When the diaphragm 32 is placed face-to-face against an object, such as the skin of a patient, the diaphragm 32 will vibrate in response to vibrations ("sounds") within the object. Accordingly, the vibrations of the diaphragm 32 cause sound waves in the air within the drum 34. These sound waves are transmitted through the stem 38 and into the acoustic tubing 40. The drum and stem of the chestpiece may be made of various materials, such as aluminum, stainless steel, titanium and/or brass.

The acoustic tubing 40 is a flexible hollow tube that connects the headset 20 to the chestpiece 30. In the stethoscope 10, the acoustic tubing 40 is branched to have a Y-shape with three ends 42, 44, 46 that are each connected by an open passageway there through. The acoustic tubing 40 is airtight to improve sound transmission from chestpiece 30 to the earpieces 24. In addition, the acoustic tubing 40 forms an air tight seal around the earpieces and stem, such as acoustic tubing end 42 forming a seal about the outer surface of a first eartube 22, acoustic tubing end 44 forming a seal about the outer surface of a second eartube 22, and acoustic tubing end 46 forming a seal about the outer surface of the chestpiece stem 38. Accordingly, vibrations in the diaphragm 32 are transmitted through the air within the open passageway that extends from the chestpiece 30, through the stem 38, the acoustic tubing 40, the eartubes 22 and the earpieces 24 to the ears of a medical professional.

In accordance with various embodiments, the flexible acoustic tubing 40 of the stethoscope 10 may be separated into segments. Some embodiments of the acoustic tubing 40 may have a first tubing segment that disconnectable from, and connectable to, a second tubing segment. For example, the flexible acoustic tubing 40 may include a first tubing segment connected to the headset 20 and a second tubing segment connected to the chestpiece 30, such that the first tubing segment is manually disconnectable from the second tubing segment at various points along the acoustic tubing. Arrows are used to illustrate a few exemplary points at which the acoustic tubing 40 may be disconnected. Arrows 12 are directed to a point within the acoustic tubing 40 near the chestpiece 30, arrows 14 are directed to a point within the acoustic tubing 40 just below the branches 47, 48, and arrows 16, 18 are directed to a point in each of the branches 47, 48. Embodiments may provide for disconnection at these or other points, and may provide for disconnection at one or more points.

Figure 2A:
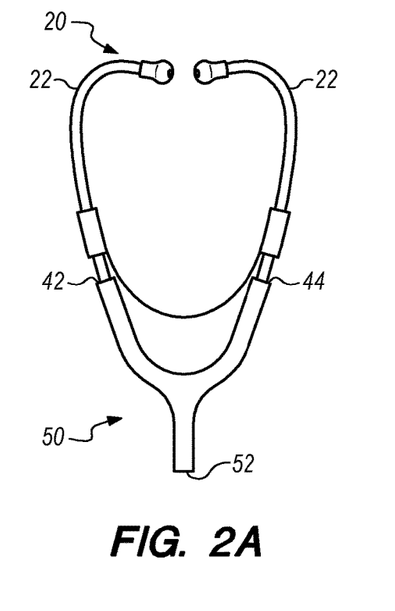
FIGS. 2A and 2B are diagrams of a stethoscope with the chestpiece disconnected from the headset.
Figure 2B:
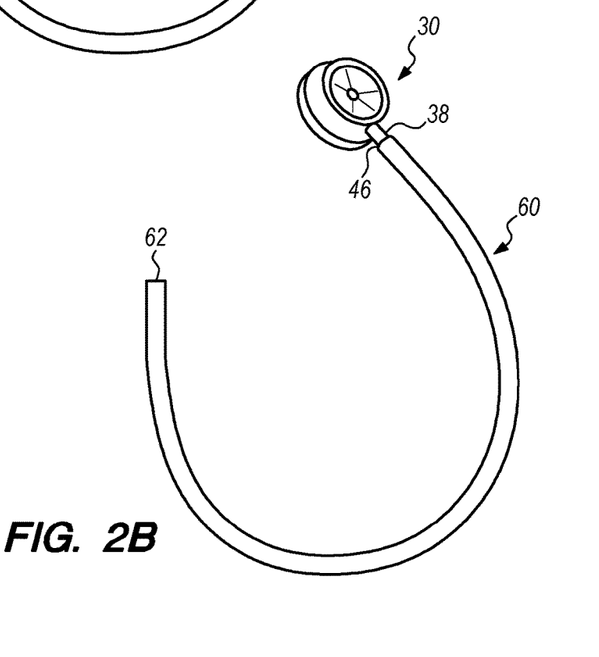

FIGS. 2A and 2B are diagrams of the stethoscope 10 with the headset 20 (shown in FIG. 2A) disconnected from the chestpiece 30 (shown in FIG. 2B) at a single point within the acoustic tubing 40. Accordingly, the acoustic tubing 40 is separable into a first tubing segment 50 connected to the headset 20 (shown in FIG. 2A) and a second tubing segment 60 connected to the chestpiece 30 (shown in FIG. 2B). The first tubing segment 50 includes one proximal end 42 that is secured to a first eartube 22, another proximal end 44 that is secured to a second eartube 22, and a distal end 52 that is manually connectable to the second tubing segment 60. The second tubing segment 60 includes one distal end 46 that is secured to the stem 38 of the chestpiece 30 and a proximal end 62 that is manually connectable to the first tubing segment 50. As describe in greater detail to follow, the first and second tubing segments 50, 60 are made to align and seal, thereby forming an acoustic passageway extending from the chestpiece 30 through the first and second tubing segments 50, 60 and the first and second eartubes 22 to the first and second earpieces 24.

Figure 3A:
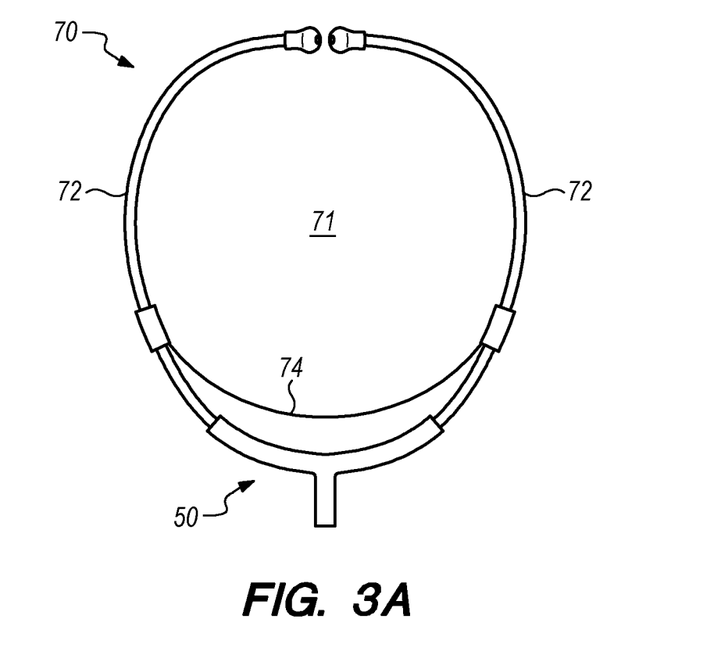
FIGS. 3A and 3B are diagrams of a headset collar.
Figure 3B:
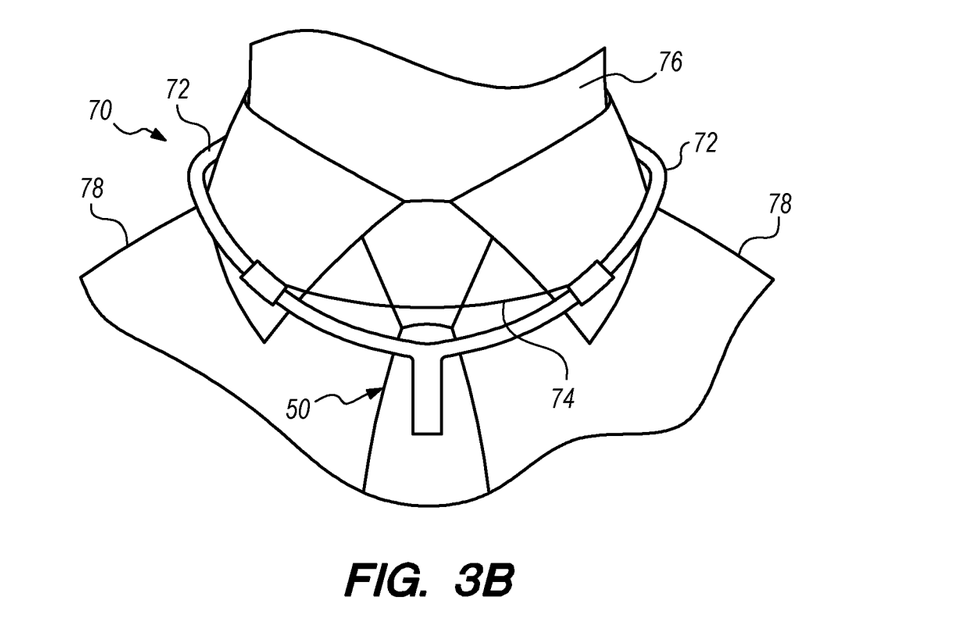

FIGS. 3A and 3B are diagrams of a headset collar 70. The headset collar 70 functions to transmit sounds to the ears of a medical professional in the same manner as the headset 20 of the stethoscope 10. In reference to FIG. 3A, the headset collar 70 has a generally circular shape, forming a generally circular opening 71 between the two eartubes 72 and the binaural spring 74. However, the opening 71 may have another shape adapted to laying comfortably about a medical professional's neck. The first tubing segment 50 may be the same as in FIG. 2A. In reference to FIG. 3B, the headset collar 70 is illustrated being worn about the neck 76 of a medical professional. As shown, the headset collar 70 preferably does not press against the skin but lays about the neck 76 and shoulders 78. Notice that the first tubing segment 50 is disconnected from the second tubing segment 60 (see FIG. 2B). In this configuration, the headset collar 70 does not support the weight of the chestpiece 30 (see FIG. 2B) and the first tubing segment 50 does not have enough length to be hung around the neck and shoulders.

Figure 4A:
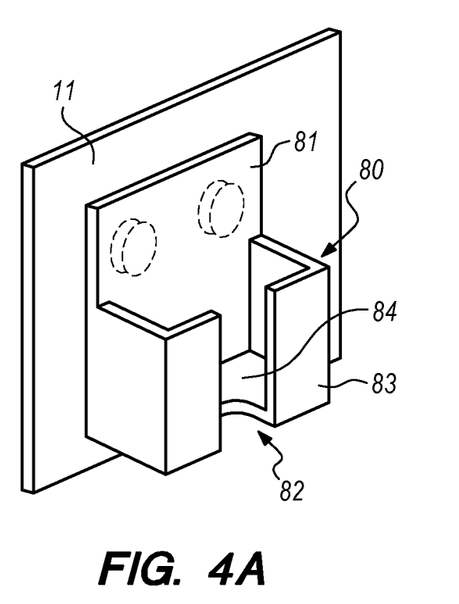
FIGS. 4A and 4B are diagrams of a chestpiece cradle.
Figure 4B:
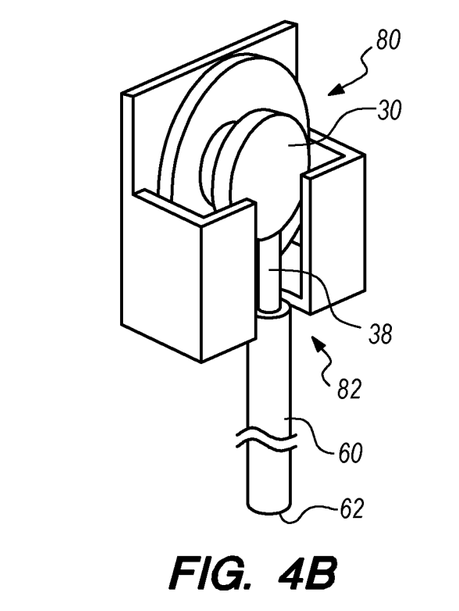

FIGS. 4A and 4B are diagrams of a chestpiece cradle 80. In reference to FIG. 4A, the cradle 80 may have a back wall 81 for securing to a flat vertical surface 11 that is available. For example, the surface 11 may be a wall in a patient room or a part of a patient bed. The cradle 80 also has an open top and a slot 82 extending down a center of a front wall 83 and along a bottom wall 84 at least partially toward the back wall 81 of the cradle. In reference to FIG. 4B, the cradle 80 is sized to receive a chestpiece 30 having a stem 38 and connected acoustic tubing segment 60. As shown, the cradle 80 allows the stem 38 and the connected acoustic tubing segment 60 to extend through the slot 82 and hang downwardly from the cradle 80. The end 62 of the tubing segment 60 will simply hang from the chestpiece 30. It should be recognized that a suitable cradle may have other shapes and configurations so long as it supports the chestpiece and makes it easy to remove the chestpiece. For example, the walls of the cradle may be contoured to complement the shape of the chestpiece.

Figure 5A:
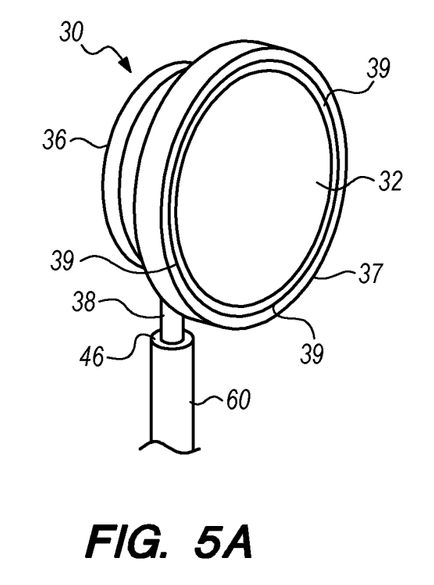
FIGS. 5A and 5B are diagrams a chestpiece having a magnet inset into a rim of the chestpiece.
Figure 5B:
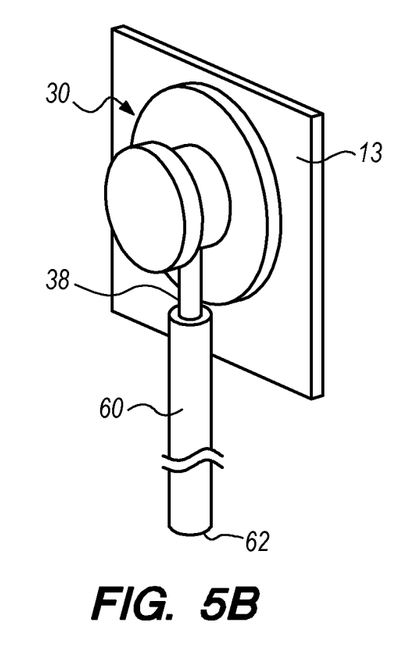

FIGS. 5A and 5B are diagrams a chestpiece 30 having a magnet 39 inset into a rim 37 of the chestpiece 30. In reference to FIG. 5A, the magnet 39 may encircle the diaphragm 32. Also shown in FIG. 5A, the chestpiece 30 illustrates the bell 36, the stem 38, and the tubing segment 60 with its distal end 46 secured to the stem 38. In reference to FIG. 5B, the chestpiece is shown magnetically secured to a metal plate 13, which may be a metal plate fixed to a wall for this very purpose or may be a component of a patient bed or other apparatus.

Figure 6A:
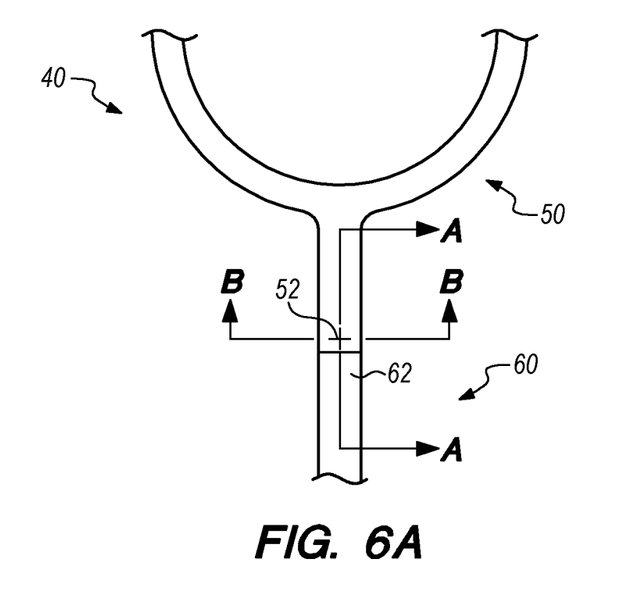
FIGS. 6A-6C are diagrams of the acoustic tubing of a stethoscope having a pair of embedded magnetic connectors according to one embodiment.
Figure 6B:
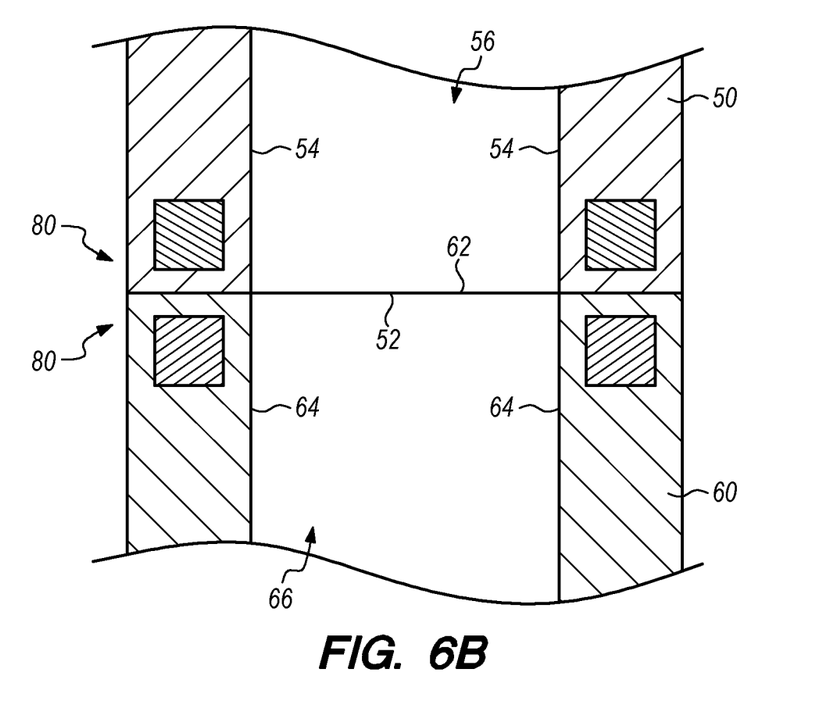
Figure 6C:
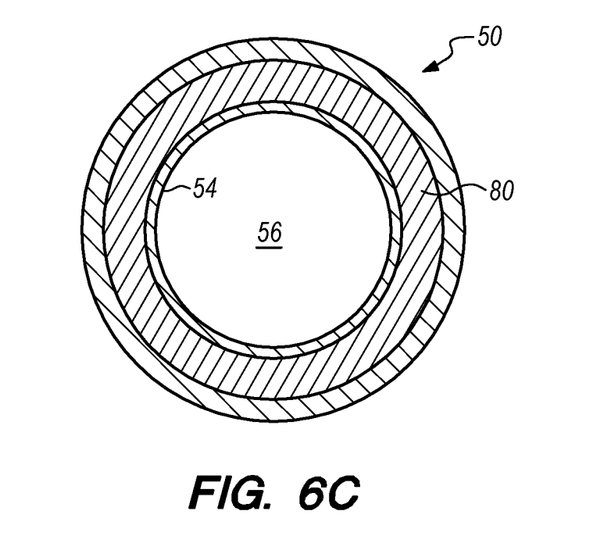

FIGS. 6A-6C are diagrams of an acoustic tube 40 of a stethoscope having a pair of embedded magnetic rings 80 (see FIG. 6B) according to one embodiment. In reference to FIG. 6A, the acoustic tube 40 includes the first tubing segment 50 (only partially shown) with a distal end 52 and the second tubing segment 60 (only partially shown) with the proximal end 62. A cross-section along line A-A is shown in FIG. 6B and a cross-section along line B-B is shown in FIG. 6C.

In reference to FIG. 6B, the first tubing segment 50 has tube walls 54 leaving an open passageway 56 extending through the entire first tubing segment 50 to the distal end 52. Similarly, the second tubing segment 60 has tube walls 64 leaving an open passageway 66 extending through the entire second tubing segment 60 to the distal end 62. When the first tubing segment 50 is aligned with the second tubing segment 60 as shown, the open passageway 56 in the first tubing segment 50 is in open acoustic communication with the open passageway 66 in the second tubing segment 60. Furthermore, in this aligned position, the magnetic ring 80 in the first tubing segment 50 is aligned with the magnetic ring 80 in the second tubing segment 60, such that a magnetic pull (force) between the two magnetic rings 80 draws the ends 52, 62 of the first and second tubing segments 50, 60 into contact. The contact between the ends 52, 62 is preferably continuous contact of the tubing material around the entire circumference of the tubing segments 50, 60 to form an airtight seal there between.

The magnetic rings 80 may be magnetic elements. As used herein, the term "magnetic elements" refers to two object that are attracted to each other as a result of a magnetic force. At least one of the magnetic elements should be a permanent magnet. However, in some embodiments the first and second magnetic elements may both be permanent magnets, and in some other embodiments one of the first and second magnetic elements may be a permanent magnet and the other of the first and second magnetic elements may be a ferromagnetic material, such as iron, cobalt, nickel and most of their alloys.

The magnetic rings 80 may be embedded into the walls 54, 64 near the ends 52, 62 of the first and second tubing segments 50, 60 by injection molding the acoustic tubing material around the ring-shaped magnetic element disposed in an injection mold. Alternatively, the magnetic elements may be embedded into the ends 52, 62 of the first and second tubing segments 50, 60 by forming a ring-shaped track in the end of an acoustic tube, positioning the ring-shaped magnetic element 80 into the track, then adhering or applying a layer of the acoustic tubing material over the circular end of the tubing segment. Either method of manufacture may lead to the configuration shown in FIGS. 6B and 6C.

FIG. 6C is a cross-sectional diagram along line B-B in FIG. 6A. One of the magnetic elements 80 is shown with the acoustic tubing material on all sides of the magnetic element 80. The inner surface of the wall 54 defines the open passageway 56 that extends through the first tubing segment 50.

FIGS. 7A-7D are diagrams of the acoustic tubing 40 of a stethoscope having a pair of push-to-connect fittings 90 that include magnetic elements 80 according to another embodiment. One of the push-to-connect fittings 90 is secured to the end 52 of the first tubing segment 50 and another of the push-to-connect fittings 90 is secured to the end 62 of the second tubing segment 60.

Figure 7A:
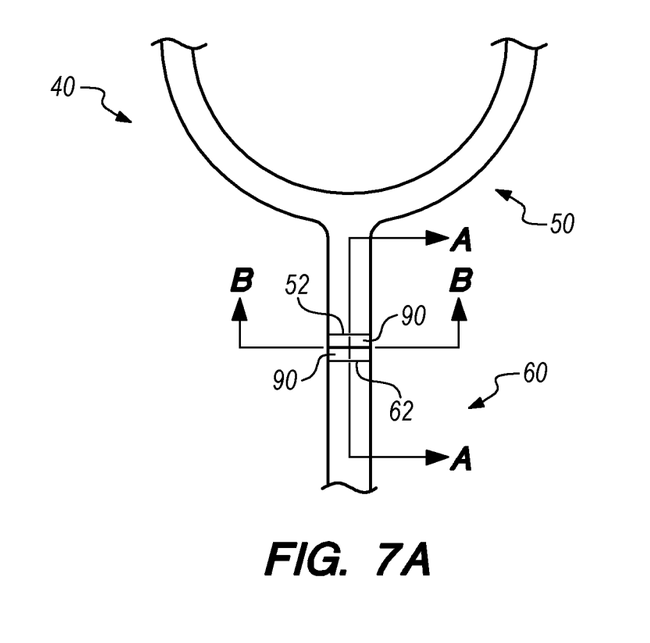
FIGS. 7A-7D are diagrams of the acoustic tubing of a stethoscope having a pair of push-to-connect fittings that include magnetic elements according to another embodiment.
Figure 7B:
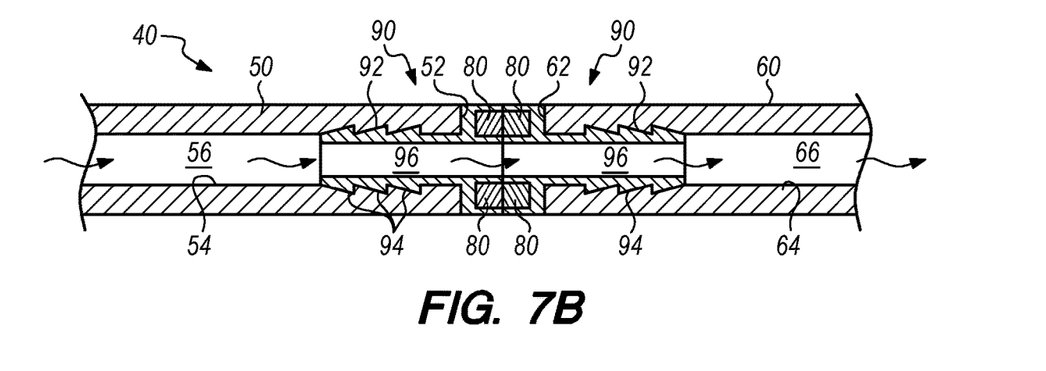

FIG. 7B is a cross-sectional diagram of a portion of the acoustic tubing 40 that includes the two push-to-connect fittings 90 as viewed along line A-A. Each push-to-connect fitting 90 includes a stem 92 having a plurality of circumferential barbs 94 formed along the outer surface of the stem 92. The ends 52, 62 of the respective tubing segments 50, 60 are manually slidable over the stems 92, such that the stems are receiving within the inner walls 54, 64 of the tubing. The walls of the tubing may be stretched slightly in order to fit over the stem such that the tubing exerts some pressure against the outside of the stem. Once the tubing segments are received over the stem, the barbs 94 oppose the tubing segments from sliding off the stems.

Each push-to-connect fitting 90 further includes a head portion that secures a magnetic element, such as the magnetic ring 80. In this non-limiting illustration, the magnetic element 80 in each push-to-connect fitting 90 is received within the head portion of the fitting but may be exposed for contact with an adjacent fitting. Furthermore, each push-to-connect fitting 90 has a passageway 96 extending axially through the fitting. Accordingly, a continuous acoustic passageway is provided through the acoustic tubing 40. For example, a continuous acoustic passageway may include the passageway 56 through the first tubing segment 50, the two passageways 96 through the two push-to-connect fittings 90, and the passageway 66 through the second tubing segment 60.

Figure 7C:
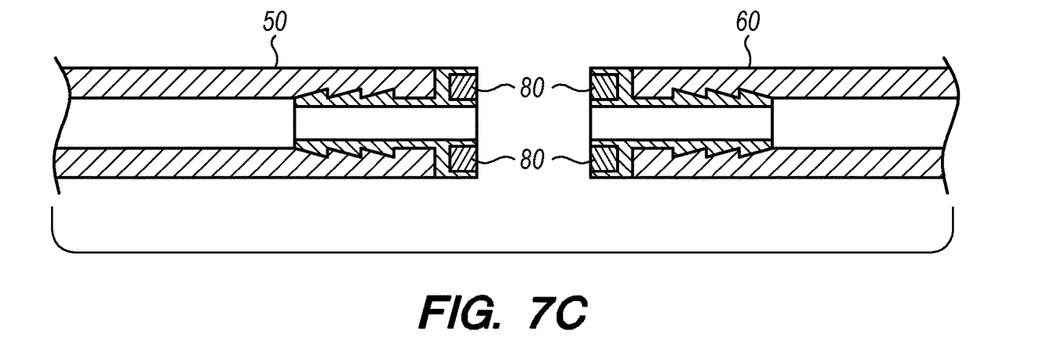

FIG. 7C is a cross-sectional diagram of the portion of the acoustic tubing 40 including the two push-to-connect fittings 90 shown in FIG. 7B. However, in FIG. 7C, the two push-to-connect fittings 90 have disconnected by applying a pulling force and/or tilting force across the interface between the two fittings. Such pulling and/or tilting force must be sufficient to overcome the magnetic pull force that draws the two magnetic elements 80 together. The first and second tubing segments 50, 60 may be connected again, as desired, by simply allowing the magnetic elements 80 of the two push-to-connect fittings 90 to come into close proximity such that a magnetic pull force between the magnetic elements 80 will bias the fittings into aligned contact.

Figure 7D:
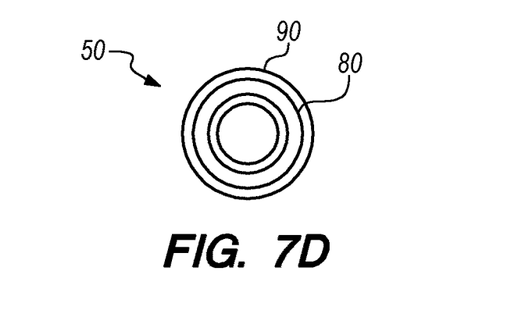

FIG. 7D is a plan view of one end of the first tubing segment 50 where all that can be seen is the face of the push-to-connect fittings 90. The magnetic element 80 may be a circular ring that is centered on the circular face of the fitting. FIG. 7D is also representative of the other fitting 90 secured to the second tubing segment 60 (see FIG. 7C.).

Accordingly, when the two magnetic elements are aligned, the first and second tubing segments 50, 60 will also be aligned.

Figure 8A:
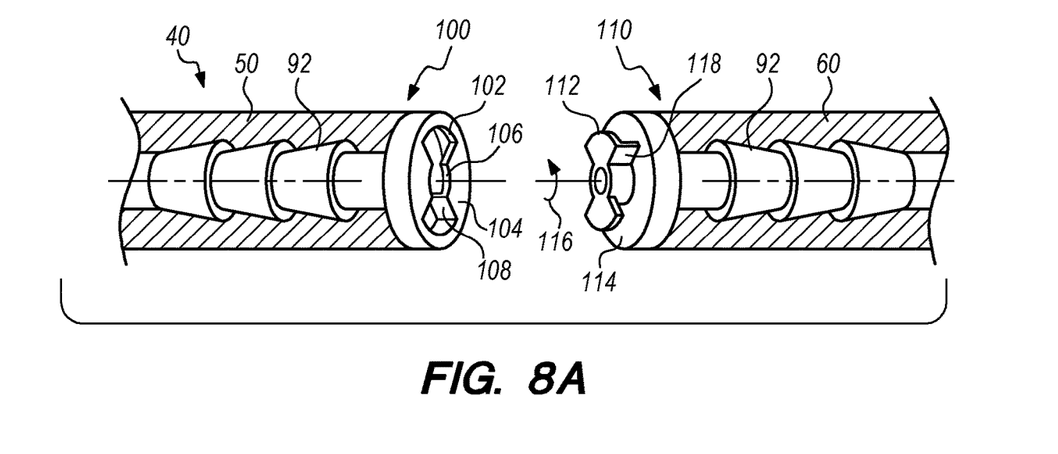
FIGS. 8A-8D are diagrams the acoustic tubing of a stethoscope having a pair of quarter-turn connectors according to a further embodiment.

FIGS. 8A-8D are diagrams a portion of the acoustic tubing 40 of a stethoscope having a pair of quarter-turn connectors 100, 110 according to a further embodiment. FIG. 8A is a partial cross-sectional perspective view of the connectors 100, 110 securing respective tubing segments 50, 60. The connectors 100, 110 may have stems 92 that are configured and used in the same manner as described in reference to FIGS. 7B-7C to secure the tubing segments 50, 60 to the connectors 100, 110. However, a head portion of a first connector 100 includes a socket 102 configured to receive a lock plate 112. In order to connect the two connectors 100, 110, the connectors 100, 110 moved together in alignment until the lock plate 112 is received into the socket 102 and the face 104 on the first connector 100 comes into contact with the face 114 on the second connector 110. Next, one or both of the connectors 100, 110 are twisted or turned about their axis to produce a relative rotation of about a quarter of a turn (see rotational arrow 116) until the connectors are locked against disconnection. A detent (see FIG. 8B) may be used to oppose accidental counter-rotation of the lock plate 112 relative to the socket 102. The geometry of the socket and lock plate may vary widely to accomplish a secure quarter-turn connection.

Figure 8B:
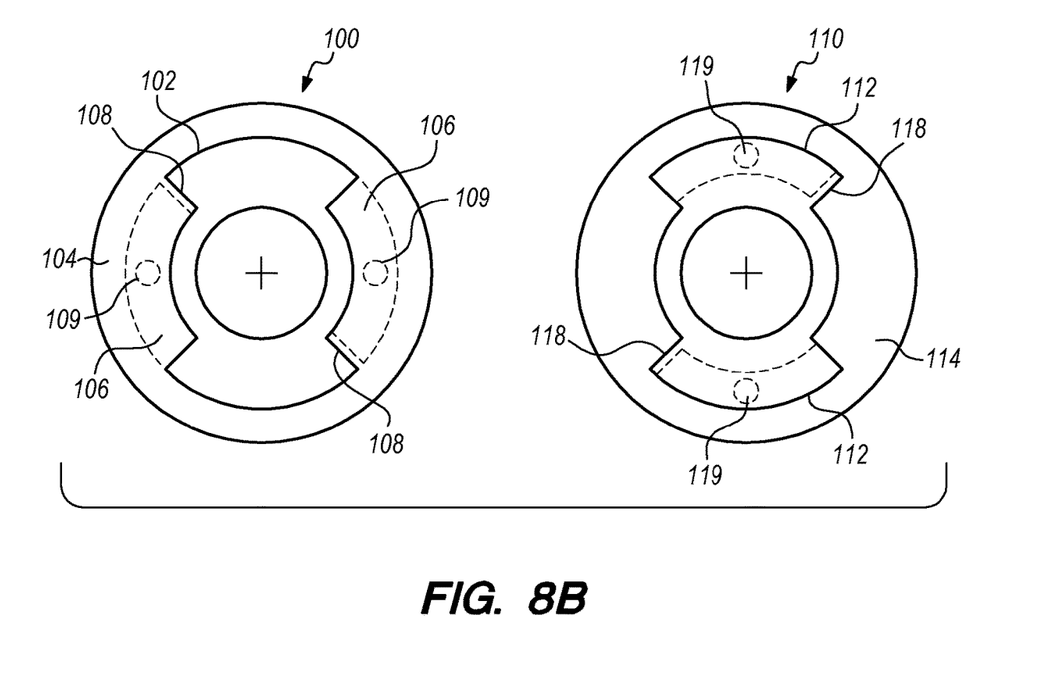

FIG. 8B are plan views of the face 104 of the first connector 100 and the face 114 of the second connector 110. On the left, the face 104 of the first connector 100 includes the socket 102. The socket 102 opening undercuts a plate 106 to form a slot under the plate 106 for receiving the lock plate 112 when inserted into the socket and rotated. The socket 102 may include a stop plate 108 and/or the lock plate 112 may include a stop plate 118 that prevents over-rotation of the lock plate 112 within the socket 102. In addition, a first detent 109 (such as a recess or dimple) may be formed in the underneath side of the plate 106 and a complementary second detent 119 (such as a projection or bump) in the underneath side of the lock plate 112. When the lock plate 112 is in a locked position in the socket 102, the first detent 109 and the second detent 119 are aligned and serve to resist counter-rotation. Each first connector 100 may have a socket 102 with two plates 106 and each second connector 110 may have pair of lock plates 112 so that the connector lock on two sides (180 degrees apart).

Figure 8C:
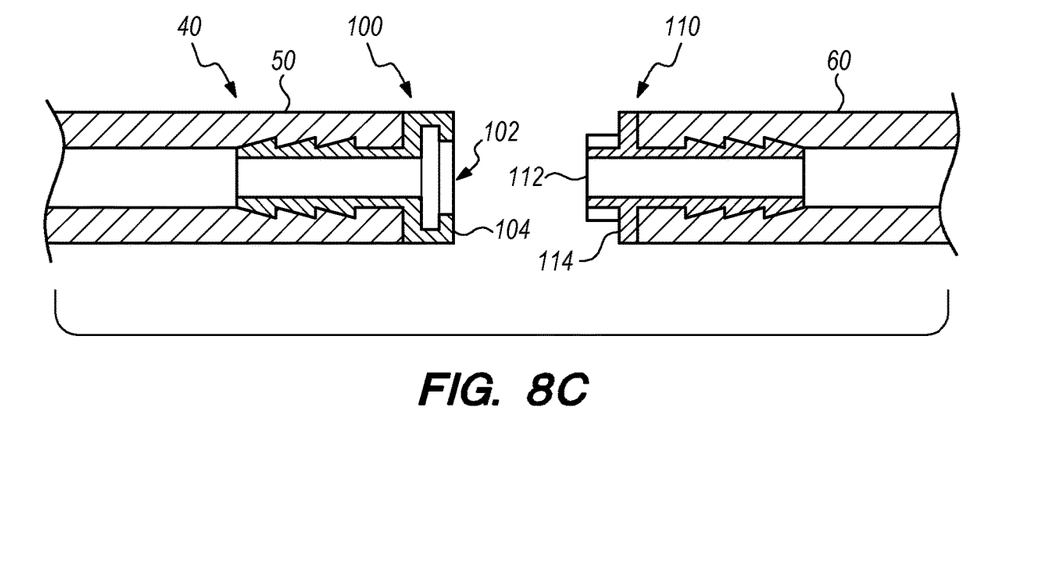
Figure 8D:
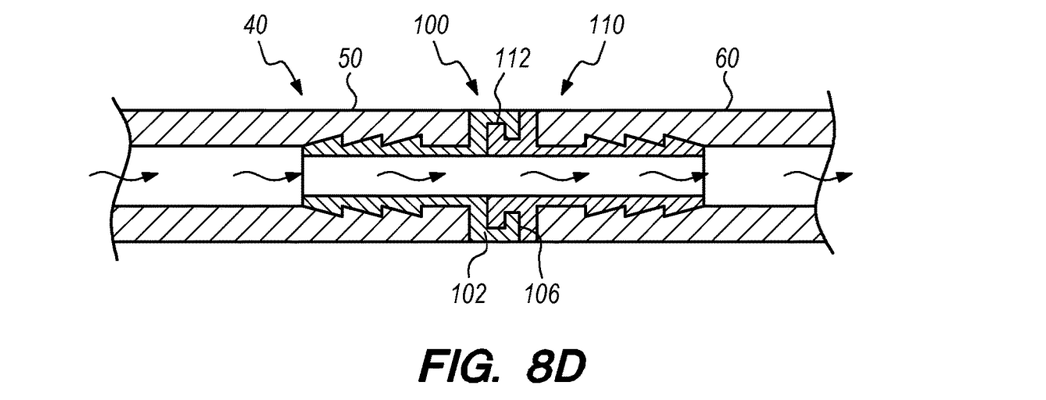

FIG. 8C is a cross-sectional view of the portion of the acoustic tubing 40 shown in FIG. 8A with the connectors 100, 110 disconnected, but align for connecting. In FIG. 8C, the lock plate 112 is aligned for insertion into the socket 102. In FIG. 8D, the lock plate 112 has been inserted and rotated within the socket 102. Accordingly, the lock plate 112 of the second connector 110 extends under the plate 106 of the first connector 100 to prevent accidental disconnection of the connectors.

Figure 9A:
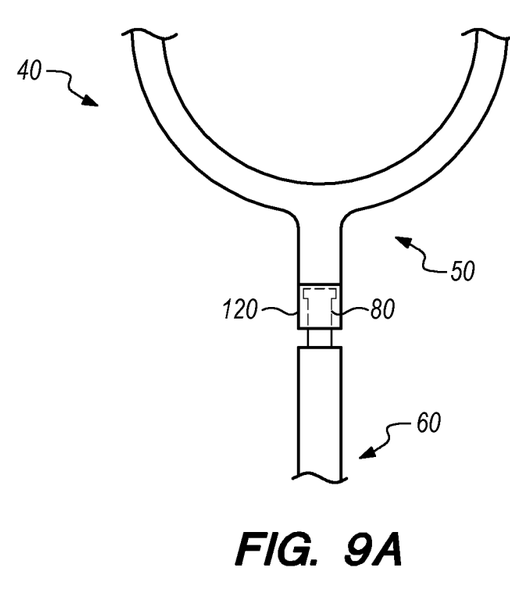
FIGS. 9A-9D are diagrams the acoustic tubing of a stethoscope having a pair of luer type connectors according to yet another embodiment.

FIGS. 9A-9D are diagrams of the acoustic tubing 40 of a stethoscope having a pair of luer type connectors 120, 130 according to yet another embodiment. As shown in FIG. 9A, a first connector 120 is secured to the first tubing segment 50 and a second connector 130 is secured to the second tubing segment 60.

Figure 9B:
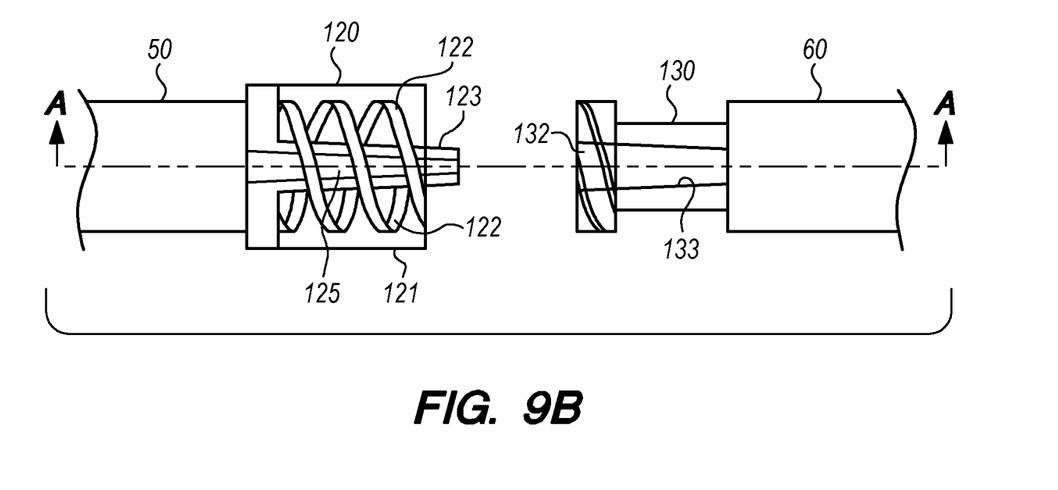

In FIG. 9B, the luer type connectors 120, 130 are shown in more detail. These connectors may also be known as luer slip connectors and slip tip connectors. A first luer connector 120 is illustrated as being made with a clear plastic, such as features may be seen through the generally cylindrical sidewall 121. For example, the cylindrical sidewall 121 includes a set of double threads 122 along the inner surface of the cylindrical sidewall 121. The double threads 122 are designed to simultaneously engage a pair of slots 132 (only one shown) about the outer perimeter of a tip of the second connector 130. The pitch of the double threads 122 and the pair of slots 132 are the same and the dimensions are complementary, such that the two slots 132 are slidably engageable with the double threads 122 to form a threaded connection there between.

Furthermore, the first connector 120 includes a tapered male tip 123 with an open passageway 125 along a central axis, and the second connector 130 includes a tapered female socket 133 with an open passageway 135 along its central axis. The outer surface of the tapered male tip 123 preferably has the same pitch as the inner surface of the tapered female socket 133 to form a seal there between when the connectors 120, 130 are fully connected.

Figure 9C:
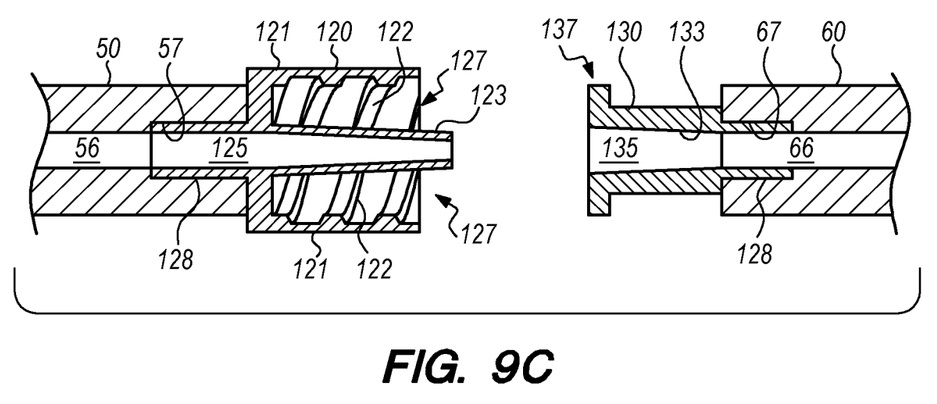

FIG. 9C is a cross-sectional view of the connectors 120, 130 in FIG. 9B as viewed along line A-A. In this view it is shown that the passageway 125 through the first connector 120 is aligned for open communication with the passageway 56 in the first tubing segment 50 and the passageway 135 through the second connector 130 is aligned for open communication with the passageway 66 in the second tubing segment 60. Furthermore, the socket 120 has an annular space 127 inside the cylindrical sidewall 121 but outside the tapered male tip 123. The annular space 127 is adapted to receive the cylindrical end 137 of the second connector 130 for threaded engagement.

The connectors 120, 130 are also illustrated with an optional cylindrical stem 128 that may be adhesively secured to the acoustic tubing without the use of barbs. Accordingly, an adhesive is disposed between the outer surface of the stem 128 and an inner surface of the tubing 50, 60. FIG. 9C further illustrates an optional recessed walls 57, 67 section that receive the stems 128.

Figure 9D:
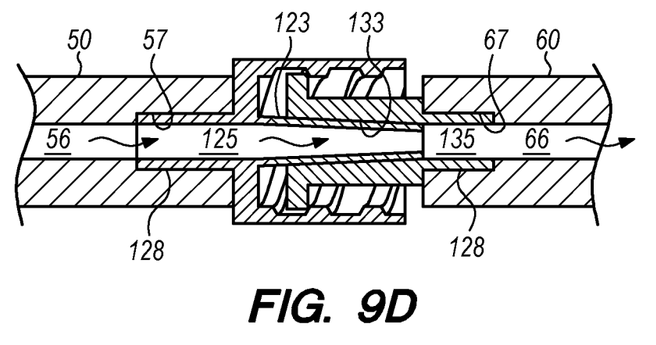

FIG. 9D is a cross-sectional view of the connectors 120, 130 as shown in FIG. 9C with the second connector 130 threadably engaged with the first connector 120 and with the threads rotatably advanced until the tapered outer surface of the male tip 123 seats and seals against the inner surface of the female socket 133. Accordingly, the configuration provides a continuous passageway 56, 125, 135, 66 there through.

The terminology used herein is for the purpose of describing particular embodiments only and is not intended to limit the scope of the claims. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof. The terms "preferably," "preferred," "prefer," "optionally," "may," and similar terms are used to indicate that an item, condition or step being referred to is an optional (not required) feature of the embodiment.

The corresponding structures, materials, acts, and equivalents of all means or steps plus function elements in the claims below are intended to include any structure, material, or act for performing the function in combination with other claimed elements as specifically claimed. Embodiments have been presented for purposes of illustration and description, but it is not intended to be exhaustive or limited to the embodiments in the form disclosed. Many modifications and variations will be apparent to those of ordinary skill in the art after reading this disclosure. The disclosed embodiments were chosen and described as non-limiting examples to enable others of ordinary skill in the art to understand these embodiments and other embodiments involving modifications suited to a particular implementation.

What is claimed is:

1. A stethoscope, comprising:
a headset including a first eartube terminating in a first earpiece and a second eartube terminating in a second earpiece;
a chestpiece having a diaphragm; and
flexible acoustic tubing having a first tubing segment and a second tubing segment, wherein the first tubing segment is connected between the headset and a first luer fitting that is secured to a distal end of the first tubing segment, wherein the second tubing segment is connected between the chestpiece and a second luer fitting that is secured to a proximal end of the second tubing segment, wherein the first luer fitting is manually disconnectable from the second luer fitting, wherein the first luer fitting is manually connectable to the second luer fitting to align and seal the first and second luer fittings and form an acoustic passageway extending from the chestpiece through the first and second tubing segments, through the first and second luer fittings and through the first and second eartubes to the first and second earpieces, wherein the first and second luer fittings include a male luer fitting with a tapered male tip and a female luer fitting with a tapered female socket, and wherein the male and female luer fittings include mating threads for forming a threaded connection there between with the tapered male tip received in the tapered female socket.

2. The stethoscope of claim 1, wherein the first tubing segment is branched and includes a first proximal end connected to the first eartube and a second proximal end connected to the second eartube.

3. The stethoscope of claim 1, wherein the first luer fitting has a barbed stem that is securely received into the distal end of the first tubing segment, and wherein the second luer fitting has a barbed stem that is securely received into the proximal end of the second tubing segment.

4. The stethoscope of claim 1, wherein the first luer fitting includes a first stem that is adhesively secured in a first recess that is formed within the distal end of the first tubing segment, and wherein the second luer fitting includes a second stem that is adhesively secured in a second recess that is formed within the proximal end of the second tubing segment.

5. The stethoscope of claim 1, wherein the headset forms a generally circular collar for hanging around a user's neck when the second tubing segment has been disconnected from the first tubing segment.

6. The stethoscope of claim 1, wherein the chestpiece includes a magnet that enables to chestpiece to be secured to a metal structure when the second segment has been disconnected from the first segment.

7. The stethoscope of claim 1, wherein the flexible acoustic tubing is made with neoprene, silicone and/or polyvinylchloride.

8. A replacement component for a stethoscope, comprising:
flexible acoustic tubing having a first tubing segment connectable to a headset of the stethoscope and a second tubing segment connectable to a chestpiece of the stethoscope, wherein the first tubing segment is connectable between the headset and a first luer fitting, wherein the second tubing segment is connectable between the chestpiece and a second luer fitting, wherein the first luer fitting is manually disconnectable from the second luer fitting, and wherein the first luer fitting is manually connectable to the second luer fitting to align and seal the first and second luer fittings and form an acoustic passageway extending through the first and second tubing segments and the first and second luer fittings, wherein the first and second luer fittings include a male luer fitting with a tapered male tip and a female luer fitting with a tapered female socket, and wherein the male and female luer fittings include mating threads for forming a threaded connection there between with the tapered male tip received in the tapered female socket.

9. A kit, comprising:
a cradle having a back wall for securing to a flat vertical surface, an open top, and a slot extending down a center of a front wall and along a bottom wall at least partially toward the back wall of the cradle, wherein the cradle is sized to receive a chestpiece having a stem and connected acoustic tubing segment, and wherein the cradle allows the stem and the acoustic tubing segment to extend through the slot and hang downwardly from the cradle; and
a stethoscope comprising:
a headset including a first eartube terminating in a first earpiece and a second eartube terminating in a second earpiece;
a chestpiece having a diaphragm; and
flexible acoustic tubing having a first tubing segment and a second tubing segment, wherein the first tubing segment is connected between the headset and a first luer fitting that is secured to a distal end of the first tubing segment, wherein the second tubing segment is connected between the chestpiece and a second luer fitting that is secured to a proximal end of the second tubing segment, wherein the first luer fitting is manually disconnectable from the second luer fitting, wherein the first luer fitting is manually connectable to the second luer fitting to align and seal the first and second luer fittings and form an acoustic passageway extending from the chestpiece through the first and second tubing segments, through the first and second luer fittings and through the first and second eartubes to the first and second earpieces, wherein the first and second luer fittings include a male luer fitting with a tapered male tip and a female luer fitting with a tapered female socket, and wherein the male and female luer fittings include mating threads for forming a threaded connection there between with the tapered male tip received in the tapered female socket.

10. The stethoscope of claim 1, wherein the mating threads include double threads for forming the threaded connection.

11. The stethoscope of claim 8, wherein the mating threads include double threads for forming the threaded connection.

12. The stethoscope of claim 8, wherein the first luer fitting has a barbed stem that is securely received into the distal end of the first tubing segment, and wherein the second luer fitting has a barbed stem that is securely received into the proximal end of the second tubing segment.

13. The stethoscope of claim 8, wherein the first luer fitting includes a first stem that is adhesively secured in a first recess that is formed within the distal end of the first tubing segment, and wherein the second luer fitting includes a second stem that is adhesively secured in a second recess that is formed within the proximal end of the second tubing segment.

14. The stethoscope of claim 9, wherein the mating threads include double threads for forming the threaded connection.

15. The stethoscope of claim 9, wherein the first luer fitting has a barbed stem that is securely received into the distal end of the first tubing segment, and wherein the second luer fitting has a barbed stem that is securely received into the proximal end of the second tubing segment.

16. The stethoscope of claim 9, wherein the first luer fitting includes a first stem that is adhesively secured in a first recess that is formed within the distal end of the first tubing segment, and wherein the second luer fitting includes a second stem that is adhesively secured in a second recess that is formed within the proximal end of the second tubing segment.

* * * * *